United States Patent
Brown et al.

(10) Patent No.: US 10,067,058 B1
(45) Date of Patent: Sep. 4, 2018

(54) AUTO-FOCUS SYSTEM

(71) Applicant: RENISHAW PLC, Wotton-Under-Edge, Glocestershire (GB)

(72) Inventors: Robert James Brown, Chepstow (GB); Ruth Alice Lawson, Stroud (GB)

(73) Assignee: RENISHAW PLC, Wotton-Under-Edge (GB)

( * ) Notice: Subject to any disclaimer, the term of this patent is extended or adjusted under 35 U.S.C. 154(b) by 0 days.

(21) Appl. No.: 15/912,919

(22) Filed: Mar. 6, 2018

(30) Foreign Application Priority Data

Mar. 6, 2017 (GB) .................................. 1703583.3

(51) Int. Cl.
| | | |
|---|---|---|
| G01N 21/00 | (2006.01) | |
| G01N 21/63 | (2006.01) | |
| G01N 21/65 | (2006.01) | |
| G02B 7/09 | (2006.01) | |
| G02B 7/34 | (2006.01) | |
| G01N 21/64 | (2006.01) | |

(52) U.S. Cl.
CPC ............ *G01N 21/63* (2013.01); *G01N 21/65* (2013.01); *G02B 7/09* (2013.01); *G02B 7/34* (2013.01); *G01N 21/64* (2013.01); *G01N 2201/068* (2013.01); *G01N 2201/06113* (2013.01)

(58) Field of Classification Search
CPC ........ G01N 21/63; G01N 21/64; G01N 21/65; G01N 15/1459; G01J 3/02; G01J 3/51; G02B 7/09; G02B 7/34
See application file for complete search history.

(56) References Cited

U.S. PATENT DOCUMENTS

| | | |
|---|---|---|
| 5,442,438 A | 8/1995 | Batchelder et al. |
| 7,202,953 B1 * | 4/2007 | Mueller ............... G01J 3/02 250/201.2 |
| 7,804,641 B2 | 9/2010 | Hammond et al. |
| 8,179,526 B2 | 5/2012 | Bennett et al. |
| 2007/0081153 A1 | 4/2007 | Hammond et al. |

OTHER PUBLICATIONS

Optophase, "ASI CRISP: Continuous Reflective Interface Sample Placement", http://www.optophase.com/Copie%20de%20CRIFF.html, downloaded Apr. 25, 2018.
Exclusive Architecture, "Autofocus Systems Part II", http://www.exclusivearchitecture.com/?page_id=1291, downloaded Apr. 25, 2018.

* cited by examiner

*Primary Examiner* — Abdullahi Nur
(74) *Attorney, Agent, or Firm* — Oliff PLC

(57) ABSTRACT

An auto-focus system suitable for a spectroscopy system uses the same illumination beam as the exciting light for spectroscopy. This is focused to a spot or line focus on the sample. An image of the spot or line focus is directed to a detector via one or more pupils located eccentrically of the optical axis, so that the focus condition is indicated by displacement of the image on the detector. The spot or line focus on the sample provides contrast in the image to enable auto-focusing without the need to observe contrast over an area of the sample. A method of scanning the surface of a sample is also described, in which a topographical map of the sample is built in a pre-scan with an objective lens having a long working distance. This enables selection of an objective with a shorter working distance for a subsequent scan.

24 Claims, 4 Drawing Sheets

AUTO-FOCUS SYSTEM

FIELD OF THE INVENTION

This invention relates to an auto-focus system, which may be used for example in a spectroscopy system. It also relates to methods of using an auto-focus system.

DESCRIPTION OF PRIOR ART

A number of techniques are known for providing auto-focusing of a sample. This can be particularly useful in a spectroscopy system, if samples with rough or uneven surface topographies are to be examined.

Photographic cameras commonly use a phase comparison technique which is passive (i.e. does not use an active light source projected onto the sample or onto the scene to be imaged). This requires that there be some contrast in the sample or scene. For many samples studied using microscopy and spectroscopy samples, this is not the case, for example a silicon sample or a pharmaceutical tablet.

Active systems are also known. For example, these may project a light beam from a light source through the objective lens of a microscope, imaging and splitting the resulting image, using trigonometric techniques to determine focus. An example is shown in U.S. Pat. No. 7,804,641 (Hammond et al/Nanometrics) and the corresponding publication US 2007/0081153. It uses a phase comparison technique with two apertures and a correlation between them. The incident beam is limited in spatial extent by imaging an aperture or field stop which forms an illumination pupil. The image of the aperture provides contrast at the sample, to enable the auto-focusing. While describing spatially constrained illumination, it is clear that a two-dimensional area is illuminated.

SUMMARY OF THE INVENTION

One aspect of the present invention provides an optical system having an auto-focus device, comprising:
- a light source;
- a focusing lens configured to receive light from the light source and focus it to a spot or line on a sample;
- a focus detection system including a detector, the focus detection system being configured to receive light from the spot or line on the sample and to direct it to the detector,
- the focus detection system having an optical axis and further comprising at least one pupil located eccentrically with respect to the optical axis, thereby producing on the detector an image of the spot or line on the sample, the image being displaced on the detector by an amount depending on distance between the focusing lens and the sample; and
- a control system configured to adjust the focus of the focusing lens on the sample in accordance with the displacement of the image of the spot or line on the detector.

This arrangement is especially suitable for a spectroscopy system. The light source may be monochromatic. The spot or line focused on the sample may cause scattering of light at shifted wavenumbers. The spectroscopy system then detects light at these shifted wavenumbers.

A second aspect of the present invention provides a spectroscopy system comprising:
- a light source;
- a focusing lens configured to receive light from the light source and focus it to a spot or line on a sample;
- a spectroscopic analyser configured to receive and spectrally analyse light from the spot or line on the sample and to pass it to a detector,
- a focus detection system including a detector, the focus detection system being configured to receive light from the spot or line on the sample and to direct it to the detector;
- the focus detection system having an optical axis and further comprising at least one pupil located eccentrically with respect to the optical axis, thereby producing on the detector an image of the spot or line on the sample, the image being displaced on the detector by an amount depending on distance between the focusing lens and the sample; and
- a control system configured to adjust the focus of the focusing lens on the sample in accordance with the displacement of the image of the spot or line on the detector.

The spectroscopic analyser may receive and analyse light which has been scattered from the spot or line focus at wavenumbers shifted from the light source, e.g. by Raman scattering.

BRIEF DESCRIPTION OF THE DRAWINGS

Preferred embodiments of the invention will now be described by way of example, with reference to the accompanying drawings, in which.

DESCRIPTION OF PREFERRED EMBODIMENTS

Figure 1:
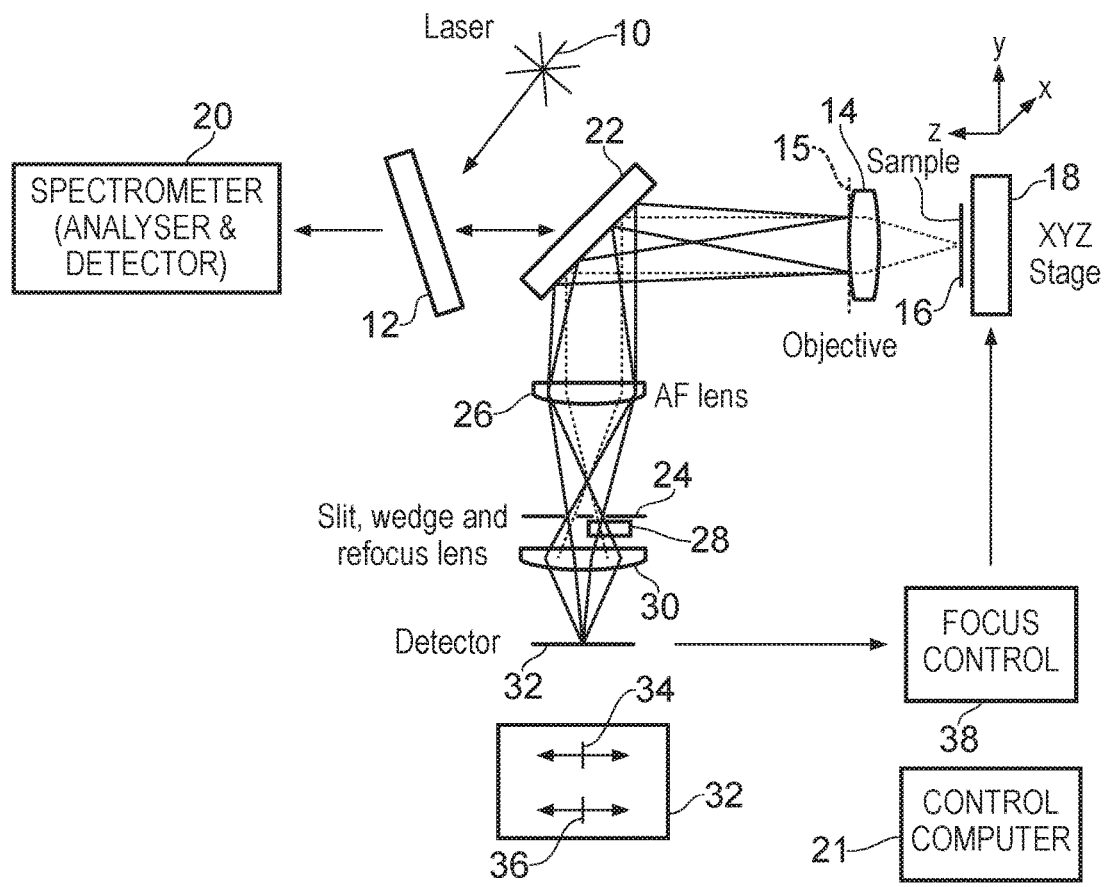
FIG. 1 is a schematic diagram of a Raman microscope spectroscopy system.

In the Raman microscope spectroscopy system of FIG. 1, monochromatic excitation light from a laser light source 10 is injected into the optical path of the Raman microscope spectroscopy system of FIG. 1 via a notch filter 12. An edge filter could be used instead. The notch filter 12 reflects the laser wavelength and transmits other wavelengths. It is placed at a low angle of incidence, e.g. 10°-15°, to allow wavelengths close to the laser wavelength to be transmitted. The beam of excitation light is expanded to fill a microscope objective lens 14, which brings it to a spot focus or line focus on a sample 16. The sample is mounted on a sample stage 18 which is motorised to move in X, Y and Z directions. This takes place under the control of a computer 21, which also controls other aspects of the operation of the system and the acquisition and processing of measurements.

Raman scattered light at wavenumbers/wavelengths which are shifted from the wavelength of the laser excitation light are collected and collimated by the microscope objective 14 and are transmitted through the notch filter 12 to a spectrometer 20. Light which is Rayleigh scattered by the sample at the laser wavelength is rejected by the notch filter. The spectrometer 20 suitably comprises a spectral analyser (e.g. a diffraction grating) and a detector (e.g. a two-dimensional CCD detector). Spectroscopic measurements are thus obtained, in a known manner. By moving the stage 18 in the X and/or Y directions under the control of the computer 21, the spot or line focus can scan an area of the sample 16 to build up a spectroscopic image of that area.

The system can also be used for other spectroscopic measurements, e.g. fluorescence or luminescence spectroscopy.

As described so far, the spectroscopy system is based upon those described in U.S. Pat. No. 5,442,438 (Batchelder et al) and U.S. Pat. No. 8,179,526 (Bennett et al), to which reference should be made for further details, and which are incorporated herein by reference. The invention may also be used with other types of spectroscopy system, e.g. absorption spectroscopy, and with systems which analyse the Rayleigh scattering (with or without spectroscopic analysis in addition).

The spectroscopy system includes an auto-focus system which will now be described.

Light at the laser wavelength is Rayleigh scattered by the sample and collimated by the objective lens 14. Part of this light is deflected by a beamsplitter 22, in order to separate it out of the main optical path of the spectroscopy system and into the optical path of the auto-focus system. The beamsplitter 22 may reflect only a small proportion of the light, e.g. 10% or 20%, to avoid any significant reduction in the Raman scattered light. Alternatively, a notch or edge filter similar to the notch or edge filter 12 could be used as the beamsplitter 22, reflecting the laser wavelength to the auto-focus system. It is also possible to arrange the spectroscopy system so that a beamsplitter transmits the laser wavelength into the optical path of the autofocus system and reflects the Raman scattered light towards the spectrometer.

The collimated light deflected into the auto-focus system is focused onto a pair of slits 24 by a lens 26. Each slit is mounted eccentrically with respect to the optical path of the auto-focus system, on opposite sides of that optical path. Each slit thus forms a pupil onto which is imaged a different eccentric portion of the back plane 15 of the microscope objective. If the laser is focused to a line on the sample 18, then the slits 14 are oriented in alignment with it so that they pass the light from the line focus. It should be noted that the slits 14 lie outside the illumination path from the light source 10 to the sample 16.

Light passing through the two slits is refocused by a refocus lens 30 onto a two-dimensional detector 32. This may for example be a CCD as shown, or a dual position sensitive detector which is cheaper, faster and easier to interpret. Two images of the spot focus or line focus on the sample are formed on the detector 32, as shown at 34, 36 (see FIG. 2 and inset in FIG. 1). A wedge or prism 28 is placed in front of or behind one of the two slits, to act as a deflector so that the two images 34, 36 are displaced one above the other in the X direction on the detector 32. The slits 24, wedge 28 and refocus lens 30 may be placed in any order along the optical path of the auto-focus system.

Figure 3:
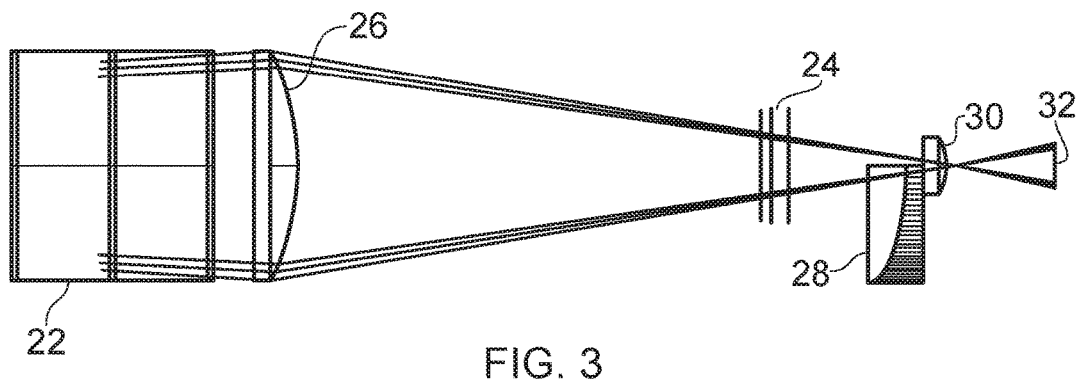
FIGS. 3, 4 and 5 are top, side and isometric ray diagrams of a focus detection system shown in FIG. 1.
Figure 4:
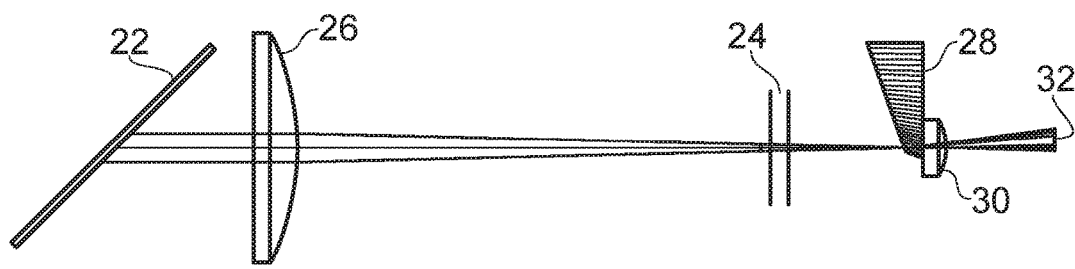
Figure 5:
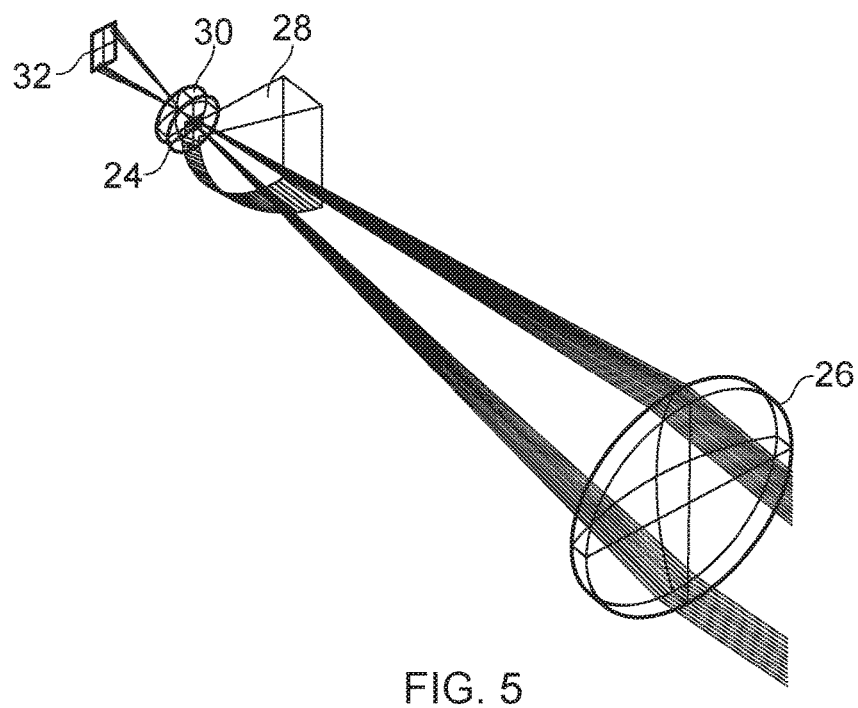

FIGS. 3, 4 and 5 further illustrate the arrangement of the auto-focus system.

Figure 2:
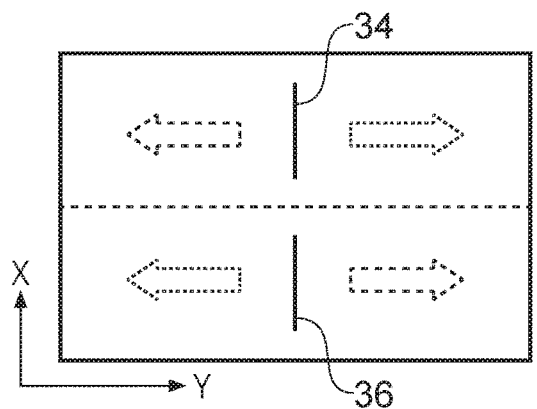
FIG. 2 is a schematic enlargement of a detector shown in FIG. 1.

In use, the focus of the laser light on the sample is adjusted by moving the XYZ stage 18 in the Z direction, relative to the objective lens 14 of the microscope. It would be possible instead to move the objective lens 14 in the Z direction. Since the slits 24 are located eccentrically with respect to the optical path, this causes the two images 34, 36 to swing in the Y direction as indicated by arrows in FIGS. 1 and 2. They swing in opposite directions since the slits 24 are on opposite sides of the optical path. The arrows in FIG. 2 are shown as dotted and broken lines respectively to indicate this.

The signals from the detector 32 are read by a focus control unit 38, which may be a software module forming part of the control computer 21 of the system or a separate unit. This is configured to detect and analyse the two signals from the two slits differentially, to determine the focus condition. If the two signals are located differently in the Y direction, this indicates that the sample is out of focus, and whether the stage 18 should be moved in the +Z or −Z direction in order to achieve focus. The focus control unit 38 feeds a signal back to the Z-axis motor of the stage 18, until the two signals are nominally in the same Y position on the detector. This forms a feedback loop which automatically keeps the excitation light in the spot or line focus on the sample surface as an X-Y scan proceeds, even if the sample has a rough or uneven surface topography. Thus the laser focus tracks the surface during the scan.

Furthermore, by recording the Z position for each X-Y position as a scan proceeds, software in the control computer 21 is optionally configured to build up a map of the three-dimensional surface topography of the sample, as a point cloud. This is facilitated by the illuminating the sample at a spot focus or line focus.

If a CCD is used as the detector 32, then in the case of a line focus the lines 34, 36 may be binned in the X direction. The resulting signal gives an average value over the line. However, for higher spatial resolution of the focus information, it possible to treat the data from each point in the line separately. In the case of a spot focus on the sample, the image of the spot on the detector may be a blurred blob when the system is out of focus. If necessary, the signal from the blurred image on the detector can also be averaged over the area of the blob.

It should be noted that U.S. Pat. No. 7,804,641 (Hammond et al/Nanometrics) does not show a spectroscopy system, but a microscope which illuminates an area of the sample, in which a pattern may be apparent. The auto-focus system described in FIGS. 1-5 above has advantages over that shown in U.S. Pat. No. 7,804,641, because it uses a spot or line focus on the sample, whereas U.S. Pat. No. 7,804,641 illuminates an area on the sample (imaging a pattern within the area, or imaging an illumination pupil aperture or field stop). In the present system, the spot or line focus provides contrast to facilitate the auto-focusing, obviating the need to observe a pattern or an illumination pupil or field stop. When in focus, the focus information is obtained from a tight focus on the sample so that, even if averaged by binning, it is not averaged over a wider illuminated area. This increases the spatial resolution of the topographic information. The focus measure is not adversely affected by features of the sample surface outside the spot or line focus currently being examined, and is less subject to surface details within the focused area.

It is also advantageous to use the same laser simultaneously for both auto-focus and spectroscopic measurements (though it is envisaged that a separate laser could be used if desired). The system described above can be used during a continuous X-Y scan, automatically tracking the focus condition and keeping the illuminated spot or line on the sample in focus throughout.

In the system described, each slit 24 forms an eccentrically located pupil causing the image of the spot or line focus to move relative to the detector, depending on the focus condition. In a simpler system, the two slits 24 could be replaced by a single eccentrically mounted slit. However, we prefer two slits since this enables differential signal processing and increases the sensitivity to the focus condition.

The slits are not essential. It is possible to use any arrangement which samples or separates one, two or more eccentric portions of the return beam, e.g. imaging one or more eccentric portions of the back plane 15 of the microscope objective. The term "pupil" as used herein should be construed accordingly. For example, the slits could be replaced by a dihedral mirror of the type used in U.S. Pat. No. 7,804,641. They could also be replaced by three or more apertures, which may yield improvements in performance but would be more complex to implement.

Figure 6:
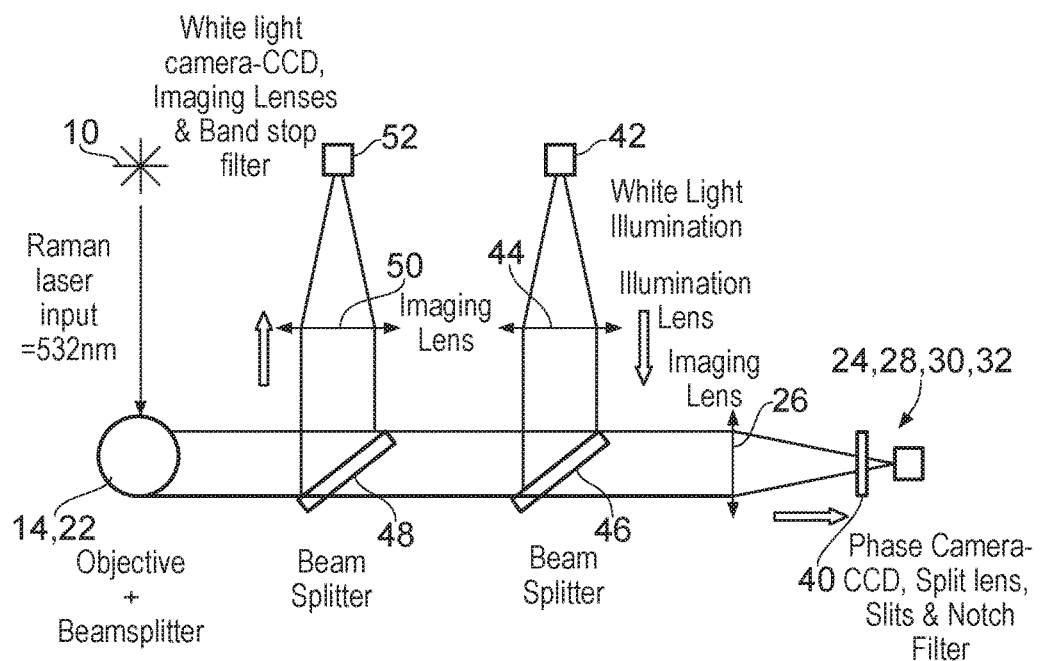
FIG. 6 is a schematic diagram of a modified Raman microscope spectroscopy system.

FIG. 6 shows a modified system, which also allows for white light illumination of the sample. This enables the user to examine an unknown sample visually, for example in order to select a particular area of interest prior to an automated spectroscopic scanning examination. To provide for auto-focus during this, the sample is simultaneously illuminated by the spectroscopic laser source 10.

In FIG. 6, components corresponding to the laser 10, microscope objective lens 14, beamsplitter 22 and to the other components 24-32 of the auto-focus system have been given the same reference numerals as in FIGS. 1-5, and need not be described further.

A white light source 42 illuminates the sample via a lens 44 and a beamsplitter 46. Light reflected from the sample is collected via a beamsplitter 48 and lens 50 to a white light camera system 52 (which may comprise a CCD sensor and imaging lenses). By adjusting the lenses 44, 50 it is possible to illuminate and examine a wide area of the sample, despite the spot or line focus of the laser illumination from the laser 10. It is desirable to include a band stop filter in the white light camera 52, to remove Rayleigh scattered light of the laser wavelength. It is also desirable to include a notch or edge filter 40 in front of the auto-focus detector 32, in order to admit only the light of the laser wavelength and exclude the white light.

Figure 7:
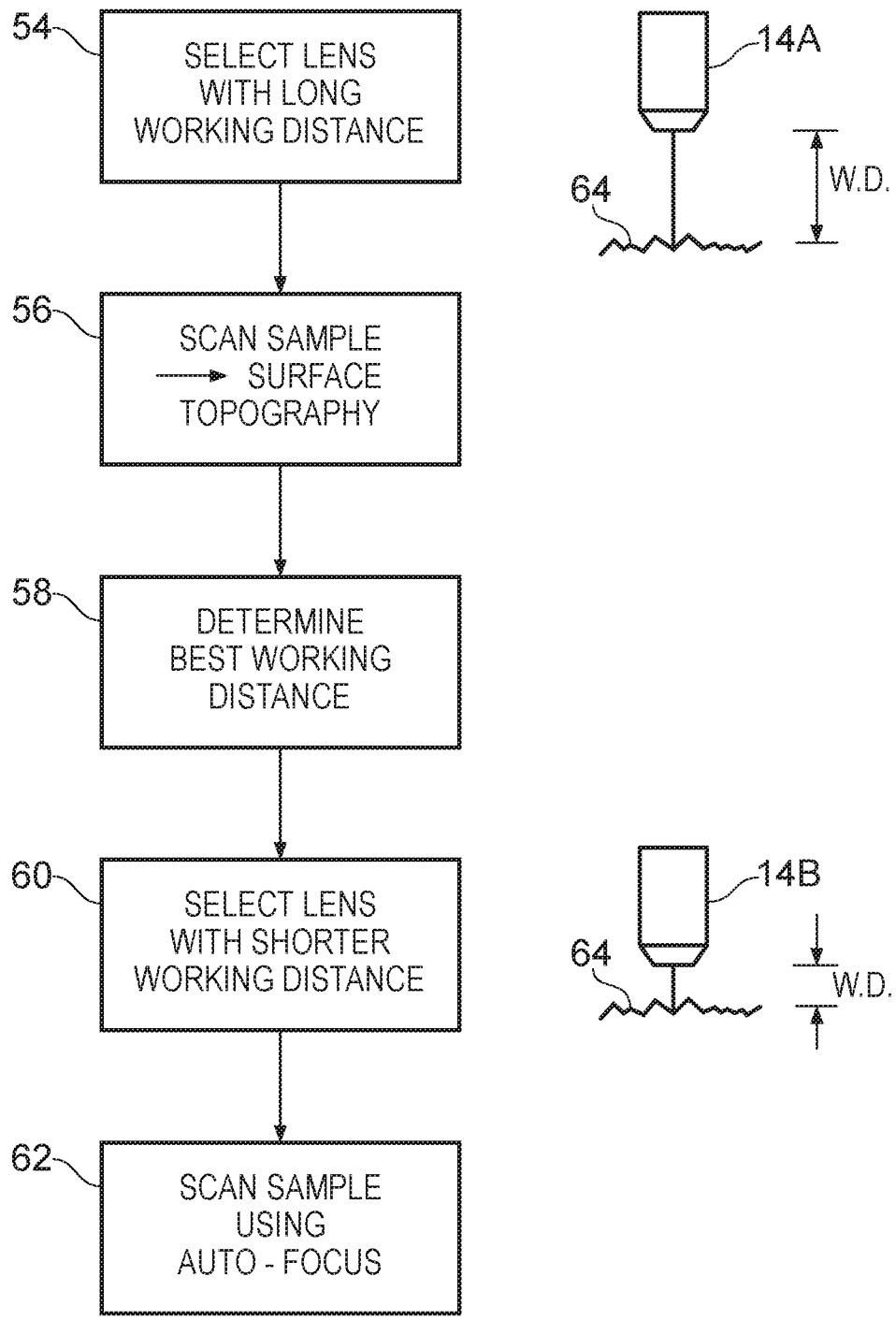
FIG. 7 is a flow chart illustrating a method of use of an auto-focus system.

FIG. 7 shows a novel method of use of the above auto-focus systems. It can also be used with other auto-focus systems such as those known in the prior art. It is particularly useful where the surface topography of the sample is rough or uneven.

In the first step 54 of this method, the user selects a microscope objective lens 14A having a long working distance W.D. and positions it on the microscope. The working distance W.D. is the space between the nose of the lens and the sample 64. Typically lenses with lower magnifications and lower numerical apertures will have longer working distances. A ×10 or ×20 lens could be selected, for example.

Next, in step 56, the control computer 21 causes the system to pre-scan the sample surface in the X-Y directions with the selected lens. This is done as described above, recording the Z position of the surface for each X-Y position as the scan proceeds. The control computer builds up a map (point cloud) of the three-dimensional surface topography of the sample.

In step 58, the control computer 21 uses the map to determine the best objective lens (i.e. shortest working distance) that can be used for a further scan of the sample in which spectroscopic measurements are taken. It may do this by comparing all the Z values in the map, to determine the maximum value. In step 60, the computer then indicates to the user a lens 14B with the next largest working distance above this maximum Z value. The best lens is thus selected which has a shorter working distance W.D. than in step 54, but which will not crash into the sample during the subsequent scan. The user fits that lens 14B in position on the microscope. A ×50 or ×100 lens could be selected, for example.

Finally, in step 62, the computer 21 controls the system to perform a scan with the selected lens 14B, taking spectroscopic measurements in a known manner. During this scan, for the most accurate results we prefer to use the above-described auto-focus system to keep the laser spot of line in focus on the sample surface. However, it would be possible for the computer 21 just to determine a scan path from the map, at a constant Z distance above the surface, and to follow that path blind.

The invention claimed is:

1. A spectroscopy system comprising: a light source; a focusing lens configured to receive light from the light source and focus it to a spot or line on a sample; a spectroscopic analyzer configured to receive and spectrally analyze light from the spot or line on the sample; a focus detection system including a detector, the focus detection system being configured to receive light from the spot or line on the sample and to direct it to the detector; the focus detection system having an optical axis and further comprising at least one pupil located eccentrically with respect to the optical axis, thereby producing on the detector an image of the spot or line on the sample, the image being displaced on the detector by an amount depending on distance between the focusing lens and the sample; and a control system configured to adjust the focus of the focusing lens on the sample in accordance with the displacement of the image of the spot or line on the detector.

2. A spectroscopy system according to claim 1, wherein the at least one pupil is located out of an illumination optical path from the light source to the sample.

3. A spectroscopy system according to claim 1, wherein the focus detection system comprises a lens configured to refocus the image of the spot or line on the detector.

4. A spectroscopy system according to claim 1, wherein a signal from the detector is averaged over the image of the spot or line.

5. A spectroscopy system according to claim 1, comprising two pupils located eccentrically with respect to the optical axis.

6. A spectroscopy system according to claim 5, wherein the control system is configured to analyse signals from the two pupils differentially.

7. A spectroscopy system according to claim 5, wherein the detector is two-dimensional, and light from the pupils is deflected relative to each other to appear one above the other on the detector.

8. A spectroscopy system according to claim 1, wherein the at least one pupil comprises a slit.

9. A spectroscopy system according to claim 7, wherein the light is focused to a line on the sample, and the slit is orientated in alignment with the line.

10. A spectroscopy system according to claim 1, wherein the control system is configured to scan across a surface of the sample, keeping the spot or line in focus on the surface during the scan.

11. A spectroscopy system according to claim 1, wherein the control system is configured to build up a topographic map of a surface of the sample.

12. A spectroscopy system according to claim 11, wherein the topographic map is built up by pre-scanning the sample using a focusing lens having a relatively long working distance with respect to the sample, and the control system is configured to determine a focusing lens with a shorter working distance for a subsequent spectroscopic scan of the sample.

13. A spectroscopy system according to claim 1, wherein the spectroscopic analyser receives and analyses light which has been scattered from the spot or line focus at wavenumbers shifted from the light source.

14. An optical system having an auto-focus device, comprising:
   a light source;
   a focusing lens configured to receive light from the light source and focus it to a spot or line on a sample;
   a focus detection system including a detector, the focus detection system being configured to receive light from the spot or line focus on the sample and to direct it to the detector;
   the focus detection system having an optical axis and further comprising at least one pupil located eccentrically with respect to the optical axis, thereby producing on the detector an image of the spot or line focus on the sample, the image being displaced on the detector by an amount depending on distance between the focusing lens and the sample; and
   a control system configured to adjust the focus of the focusing lens on the sample in accordance with the displacement of the image of the spot or line focus on the detector.

15. An optical system according to claim 14, wherein the at least one pupil is located out of an illumination optical path from the light source to the sample.

16. An optical system according to claim 14, wherein the focus detection system comprises a lens configured to refocus the image of the spot or line on the detector.

17. An optical system according to claim 14, wherein a signal from the detector is averaged over the image of the spot or line.

18. An optical system according to claim 14, comprising two pupils located eccentrically with respect to the optical axis.

19. An optical system according to claim 14, wherein the control system is configured to scan across a surface of the sample, keeping the spot or line in focus on the surface during the scan.

20. An optical system according to claim 14, wherein the control system is configured to build up a topographic map of a surface of the sample.

21. An optical system according to claim 20, wherein the topographic map is built up by pre-scanning the sample using a focusing lens having a relatively long working distance with respect to the sample, and the control system is configured to determine a focusing lens with a shorter working distance for a subsequent spectroscopic scan of the sample.

22. A method of using an optical system to scan a surface of a sample, the system comprising:
   a light source;
   a focusing lens configured to receive light from the light source and focus it to a spot or line on the sample surface;
   a focus detection system including a detector, the focus detection system being configured to receive light from the spot or line focus on the sample surface and to direct it to the detector;
   wherein the method comprises:
   using the focus detection system to build a topographic map of the sample surface, by pre-scanning the sample surface using a focusing lens having a relatively long working distance with respect to the sample surface;
   determining from the topographic map a focusing lens having a shorter working distance with respect to the sample surface; and
   subsequently scanning the sample surface using the focusing lens having a shorter working distance.

23. A method according to claim 22, wherein the focus detection system is configured to perform auto-focusing during at least the subsequent scanning.

24. A method according to claim 22, wherein the optical system is a spectroscopy system, and spectroscopic measurements are taken during the subsequent scanning.

* * * * *